United States Patent [19]

Barton et al.

[11] Patent Number: 4,471,137
[45] Date of Patent: Sep. 11, 1984

[54] HIGHLY STERICALLY HINDERED GUANIDINES AND PROCESS FOR THE PRODUCTION THEREOF

[75] Inventors: Derek H. R. Barton, Gif S. Yvette; John D. Elliott, Bures S. Yvette; Stephan D. Gero, Les Ulis, all of France

[73] Assignee: Centre National de la Recherche Scientifique (CNRS), Paris, France

[21] Appl. No.: 398,219

[22] Filed: Jul. 14, 1982

[30] Foreign Application Priority Data

Jul. 15, 1981 [FR] France ............................... 81 13755

[51] Int. Cl.$^3$ .................. C07C 129/00; C07C 128/00
[52] U.S. Cl. .................................... 564/240; 564/241; 560/116; 560/117
[58] Field of Search ................................ 564/240, 241

[56] References Cited

U.S. PATENT DOCUMENTS 3,274,230  9/1966  Braun .
3,308,094  3/1967  Sherr .................................. 260/47

FOREIGN PATENT DOCUMENTS 2019933  10/1969  France .
1208252  10/1970  United Kingdom ................ 564/240
1233420   5/1971  United Kingdom ................ 564/240

OTHER PUBLICATIONS

Sawai et al., "The Reaction of Isocyanide–Mercuric Chloride Complexes with Amines", Journal of Organometallic Chemistry, vol. 94, No. 3, Aug. 5, 1975, pp. 335 and 342.

Eilingsfeld et al., "Synthese und Reaktionen von Chloroformamidiniumchloriden", Chemische Berichte, vol. 97, No. 5, 1964, pp. 1234, 1237 and 1238.

Kessler et al., Tetrahedron Letters, vol. 26, pp. 1805–1820.

Primary Examiner—Paul J. Killos
Attorney, Agent, or Firm—Fleit, Jacobson, Cohn & Price

[57] ABSTRACT

Compounds of the formula

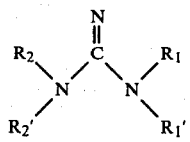

in which
$R_1$, $R_1'$, $R_2$, $R_2'$ and $R_3$ independently represent a $C_{1-6}$ alkyl radical, in addition to which $R_3$ may represent a hydrogen atom, the alkyl radicals together containing in all at least 8 carbon atoms, are provided for use as highly sterically hindered bases in chemical syntheses.

5 Claims, No Drawings

HIGHLY STERICALLY HINDERED GUANIDINES AND PROCESS FOR THE PRODUCTION THEREOF

This invention relates to new highly sterically hindered guanidines, to processes for their production and to their use in chemical syntheses.

Generally, highly sterically hindered organic bases play an important part in chemical syntheses.

Among the highly hindered strong bases, those of the amidine type are relatively few in number, but are particularly interesting in the field of syntheses. However, these amidine bases are attended by the disadvantage of being relatively expensive.

It is for this reason that the present invention seeks to provide a new series of highly hindered organic bases which may be produced from relatively inexpensive products.

More particularly, the present invention relates to a series of guanidines which are stronger and more hindered than the amidine bases hitherto used. The compounds in question correspond to the following formula:

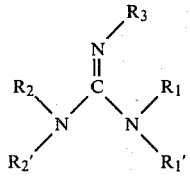
(I)

in which $R_1$, $R'_1$, $R_2$, $R'_2$ and $R_3$ independently represent a $C_1$–$C_6$ alkyl radical, in addition to which $R_3$ may represent a hydrogen atom, the alkyl radicals together containing in all at least 8 carbon atoms.

The present invention also provide highly sterically hindered guanidines of formula (I) in which $R_1$, $R_1'$, $R_2$, $R_2'$ and $R_3$ independently represent a hydrogen atom, a methy, ethyl, isopropyl or tertiary butyl radical, $R_1$, $R_1'$, $R_2$, $R_2'$ and $R_3$ together containing in all at least 8 carbon atoms, with the proviso that when the four radicals $R_1$, $R_1'$, $R_2$, $R_2'$, all represent a methyl radical or all represent an ethyl radical, then $R_3$ is not a tertiary butyl radical.

Among the substituent alkyl radicals, the methyl, ethyl, isopropyl or t-butyl radicals are mentioned in particular.

The new guanidines according to the present invention may be prepared in particular by reacting an amine corresponding to the following formula

 (II)

with a Vilsmeier salt corresponding to the following formula

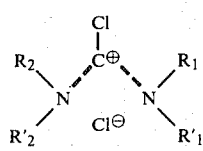
(III)

The Vilsmeier salt may be prepared by treating the corresponding tetra-alkyl urea in a solvent, particularly benzene or ether, with phosgene in toluene or in ether at 0° C.

SCHEME 1

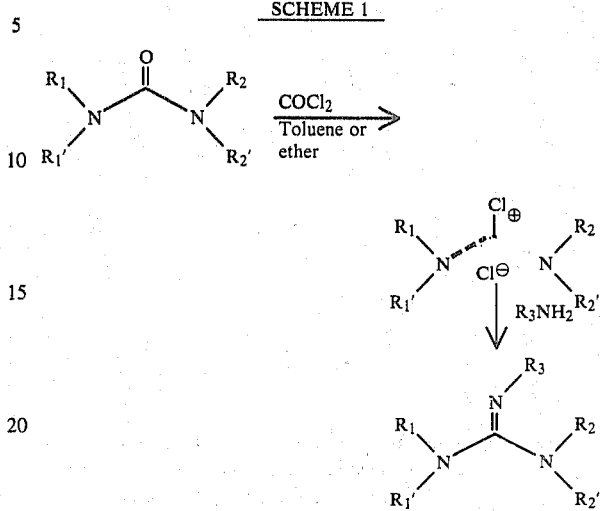

SCHEME 2

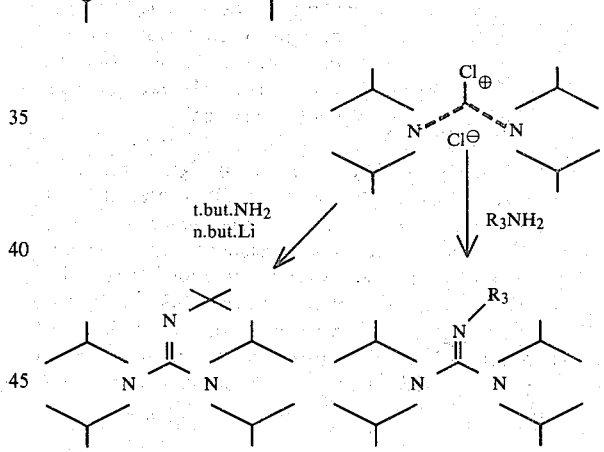

This process, which is illustrated in scheme 1, may be used in particular for producing guanidines corresponding to the following formulae:

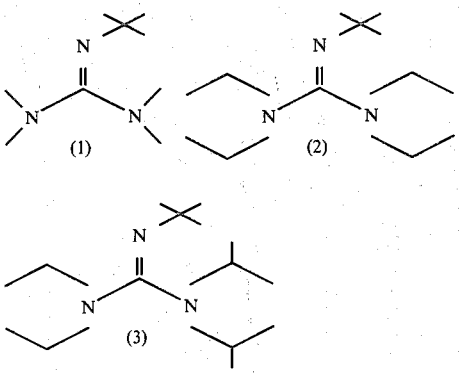

In cases where the guanidines to be prepared are more hindered, such as those corresponding to the following formulae:

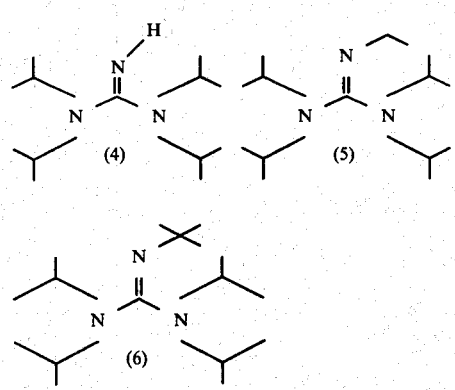

it is not possible to prepare the Vilsmeier salts from tetraisopropyl urea. Instead, they have to be prepared as shown in scheme 2 from tetraisopropyl thiourea under the same conditions as before.

With regard to the most highly hindered urea (6), it is necessary, in order to obtain a satisfactory yield of the amine over the Vilsmeier salt, to introduce the Vilsmeier salt in the form of the corresponding anion by reacting the t-butyl amine in the presence of t-butyl lithium.

The guanidines according to the present invention may be widely used in the field of chemical syntheses.

Thus, the guanidines according to the invention may be used in the production of esters by alkylating carboxylic acid amidinium salts with alkyl halides, as already described in the literature: N. Ono, T. Yanada, T. Saito, K. Tanaka and A. Kaji, Bull. Chem. Soc. Jap., (1978), 51, 2401, this process being of particular interest for the production of highly hindered carboxylic acid esters.

The carboxylic acid salts with the guanidines according to the invention lead to an extremely fast and clean reaction when they react with alkyl iodides to give the corresponding esters in very high yields.

Examples of reactions using the compounds according to the present invention are illustrated below in schemes 3 and 4:

SCHEME 3

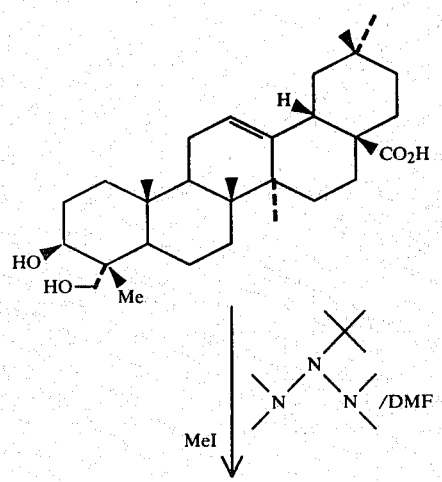

-continued
SCHEME 3

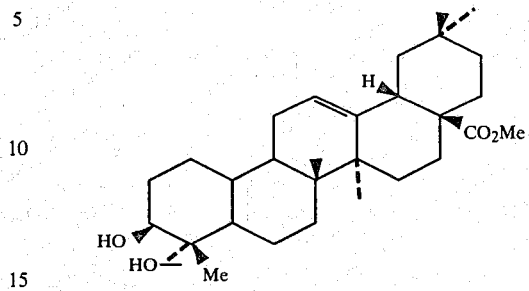

SCHEME 4

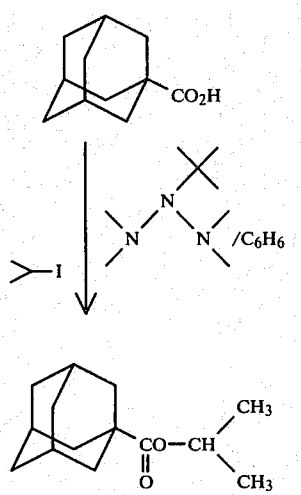

In scheme 3, the hederagenin reacts rapidly in DMF at room temperature with methyl iodide in the presence of the compound according to the invention to give the corresponding methyl ester in a yield of 88%.

In scheme 4, the adamantanoic acid reacts almost immediately in benzene in the presence of isopropyl iodide at ambient temperature to give the isopropyl derivative in a yield of 91%.

The compounds according to the invention may also be used in the preparation of Δ-2 and Δ-3-cholestene from 3-β-hydroxy cholestane tosylate.

According to the literature, this reaction takes place under reflux at 170° C. in collidine, giving a yield of 60% in 6 hours in accordance with the following scheme:

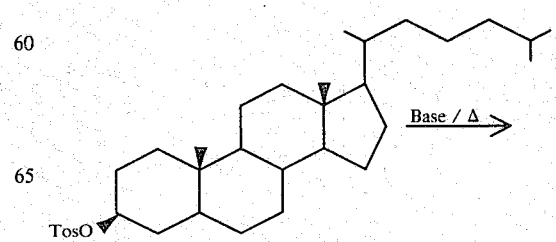

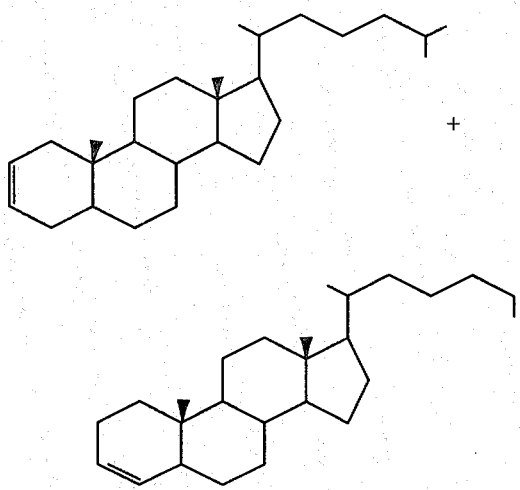

When the tosylate is heated for 24 hours at 120° C. with the guanidine (1) according to the present invention, a mixture of Δ-2 and Δ-3-cholestene is obtained in a yield of 80% after purification by column chromatography.

When the tosylate is heated for 24 hours at 120° C. with the compound of formula (3), the mixture of Δ-2 and Δ-3-cholestene is obtained in a yield of 79% after column chromatography.

It is also possible to alkylate 2,6-dimethyl phenol in a yield of 80% exclusively on the oxygen with the compound of formula (1) by way of the corresponding phenoxide, followed by the addition of methyl iodide at ambient temperature.

Alkylation of ethyl acetoacetate is also possible using the compound of formula (1) as base.

The addition of an equivalent of the compound of formula (1) to a solution of ethyl acetoacetate in ether, followed by the addition of an excess of methyl iodide, gives 83% of the mono-C-alkylated compound (a) accompanied by only traces of the dimethylated compound (b) after a reaction time of approximately 5 minutes:

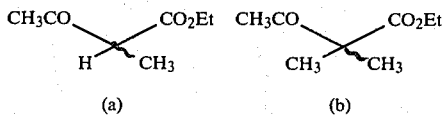

The mono-C-alkylated compound may be reconverted into the di-C-alkylated derivative (b) in a yield of 83% in the presence of another quantity of the compound of formula (1) and an excess of methyl iodide.

The following Examples are intended to illustrate other features and advantages of the invention without limiting it in any way.

EXAMPLE 1

Preparation of N-t-butyl-N',N',N'',N''-tetramethyl guanidine

A solution of 5 g (0.043 mole) of N,N,N',N'-tetramethylurea in 10 ml of dry benzene is added dropwise over a period of 10 minutes with stirring at 0° C. to a solution of 8.29 g (0.084 mole) of phosgene in 25 ml. of toluene. The mixture is heated to room temperature and then stirred for 2 hours. The solvents and the excess phosgene are evaporated, leaving the following compound

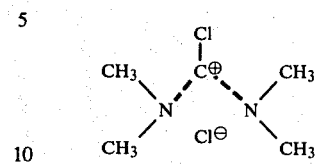

in the form of a hygroscopic white crystalline solid.

15 ml of dry t-butylamine (0.143 mole) is added with stirring to a solution of this solid in 10 ml of dry acetonitrile at a temperature of 0° C.

The mixture is heated to room temperature and then refluxed for 2 hours. The solvents are evaporated and the residue is triturated four times with 50 ml of ether.

20 ml of a 50% aqueous sodium hydroxide solution is added to the residue. After cooling of the mixture, it is extracted with 250 ml of ether. The extract is dried over anhydrous sodium sulfate, filtered and evaporated to give a pale yellow oil.

Distillation gives 6.25 g of the title compound in the form of a colourless liquid (yield 85%). This product has the following characteristics:

Bp. 760 mm 178°–183° C.

$\nu_{max}$ (liquid film) 1620 cm$^{-1}$ (C=N).

δ (CDCl$_3$): 1.22 (9H, S, N.C(CH$_3$)$_3$) and 2.67 (12H, S, (CH$_3$)$_2$N.C.N(CH$_3$)$_2$).

m/e: 171 (M+).

EXAMPLE 2

Preparation of N,N,N',N'-tetraethyl urea 100 ml of anhydrous diethyl amine (0.965 mole) are added dropwise with stirring at −78° C. to a solution of 8.72 g of phosgene (0.089 mole) in 30 ml of dry ether.

25 ml of ether are then added and the mixture is heated to room temperature and stirred for 18 hours.

The product is filtered and the residue is washed with ether. The filtrate is then evaporated, leaving an orange oil.

The product is dissolved in chloroform and the solution is washed with a 1M aqueous hydrochloric acid solution, water, a saturated sodium bicarbonate solution, water and finally with brine.

Drying over anhydrous sodium sulfate, filtration and evaporation give 14.7 g of N,N,N',N'-tetraethyl urea in the form of a chromatographically homogeneous pale yellow oil (yield 97%) having the following characteristics:

Bp.: 213°–215° C. (lit. 205° C.).

$\nu_{max}$ 2975, 2940, 2875 (C—H) and 1645 cm$^{-1}$ (C=O, urea).

δ (CDCl$_3$): 1.09 (12H, t, J=7 Hz, 4×.CH$_2$.CH$_3$) and 3.17 (8H, q, J=7 Hz, 4×.CH$_2$.CH$_3$).

m/e: 172 (M+).

EXAMPLE 3

Preparation of N-t-butyl-N',N',N'',N''-tetraethyl guanidine 39.5 g of phosgene (0.40 mole) in 100 ml of dry ether are added to 12.0 g of N,N,N',N'-tetraethyl urea (0.07 mole) and the mixture is left standing at room temperature for 24 h.

The ether and the excess phosgene are evaporated to give an orange gum which is dissolved in 10 ml of anhydrous acetonitrile.

30 ml of dry t-butyl amine (0.28 mole) are carefully added to the resulting solution cooled in an ice bath and the mixture left standing for 15 hours at room temperature.

The solvents are evaporated and the residue is triturated with ether to give a white crystalline solid. The solid is mixed with 50 ml of a 50% aqueous potassium hydroxide solution and extracted with ether. The ethereal extract is dried over anhydrous sodium sulfate, filtered and evaporated to give a pale yellow oil.

Distillation in vacuo gives 7.64 g of a colourless liquid (yield 48%). This product, which corresponds to the title compound has the following characteristics:

Bp: 60°–62° C. (0.05 mm Hg).

$v_{max}$ (liquid film): 2975, 2940, 2875 (C—H) and 1620 cm$^{-1}$ (C=N).

$\delta$ (CDCl$_3$): 1.00 (12H, t, J=7 Hz, 4×.CH$_2$.CH$_3$), 1.21 (9H, S, .C(CH$_3$)$_3$) and 3.00 (8H, q, J=7 Hz, 4×.CH$_2$.CH$_3$).

m/e: 227 (M+).

Found: C, 68.72; H, 12.82; N, 18.70; C$_{13}$H$_{29}$N$_3$. Calculated: C, 68.66; H, 12.85; N, 18.48%.

EXAMPLE 4

Preparation of N,N-diethyl-N',N'-diisopropylurea 50 ml of diethylamine (0.48 mole) are added to 5.699 g of N,N-diisopropyl carbamoyl chloride (0.035 mole) in a flask equipped with a reflux condenser. The reaction is exothermic and the mixture is left standing for 3 hours at room temperature.

The excess diethylamine is evaporated and the product is distributed between ethyl acetate and water. The organic phase is washed with aqueous 1M hydrochloric acid, water, a saturated sodium bicarbonate solution, water and finally with brine.

The solution is dried over anhydrous sodium sulfate, filtered and evaporated to give a chromatographically homogeneous (thin-layer chromatography, ether/hexane 1:1) colourless liquid.

Distillation under reduced pressure gives 4.911 g of a colourless liquid corresponding to the title compound (yield 70%) which has the following properties:

Bp.: 54°–57° C. (0.03 mmHg).

$v_{max}$ (liquid film): 1645 cm$^{-1}$ (C=O, urea).

$\delta$ (CDCl$_3$): 1.05 (6H, t, J=7 Hz, 2×CH$_2$.CH$_3$) 1.23 (12H, d, J=7 Hz, 2×CH$_3$.CH.CH$_3$) 3.02 (4H, t, J=7 Hz, 2×.CH$_2$.CH$_3$) and 3.30 (2H, septet, J=7 Hz, 2×CH$_3$.CH.CH$_3$).

m/e: 200 (M+), 185 (M+—CH$_3$), 157 (M+—C$_3$H$_7$) and 100 (M+—C$_4$H$_{10}$NO).

Found: C, 65.93; H, 12.18; N, 14.10; C$_{11}$H$_{24}$N$_2$O. Calculated: C, 65.95; H, 12.08; N, 13.99%.

EXAMPLE 5

Preparation of N-t-butyl-N',N'-diethyl-N'',N''-diisopropyl guanidine

A solution of 20 ml of phosgene (0.28 mole) in 50 ml of dry ether is added to a solution of 11.305 g (0.05 mole) of N,N-diethyl-N',N',-diisopropyl urea in 40 ml of dry ether.

The mixtue is left standing at room temperature for 9 days during which a white crystalline precipitate is formed. The ether and the excess phosgene are evaporated to give a white crystalline hygroscopic solid having the following characteristics:

$\delta$ (CDCl$_3$): 1.10 (6H, t, J=7 Hz, 2×.CH$_2$.CH$_3$) 1.27 (12H, d, J=7 Hz, 2×H$_3$C.CH.CH$_3$) 3.12 (4H, q, J=7 Hz, 2×.CH$_2$.CH$_3$) and 3.70 (2H, septet, J=7 Hz, 2×H$_3$C.CH.CH$_3$).

The product is dissolved in 20 ml of dry distilled acetonitrile and 40 ml of t-butylamine added to the resulting solution.

The mixture is heated to reflux temperature over a period of 72 hours and the solvents are evaporated. The product is thoroughly triturated with ether and then treated with a 50% aqueous potassium hydroxide solution. The mixture is extracted with ether and the ethereal extracts are washed with brine.

After drying over anhydrous sodium sulfate, filtration and evaporation, a pale yellow liquid is obtained. The product is dried over potassium hydroxide pellets and distilled in vacuo to give 8.32 g of the title compound in the form of a colourless liquid (yield 60%).

The traces of N,N-diethyl-N',N',-diisopropyl urea present are eliminated by treatment with an excess of hydrogen chloride in ether, followed by trituration of the insoluble residue with ether. The title compound is liberated using a 50% aqueous potassium hydroxide solution, followed by extraction with ether and evaporation of the ethereal extract to give a colourless liquid which has the following properties:

Bp.: 74°–77° C. (0.09 mmHg).

$v_{max}$ (liquid film): 1614 cm$^{-1}$ (C=N).

$\delta$ (CDCl$_3$): 1.03 (6H, t, J=7 Hz, 2×.CH$_2$.CH$_3$) 1.20 (12H, d, J=7 Hz, 2×H$_3$C.CH.CH$_3$) 1.23 (9H, S, .C(CH$_3$)$_3$) 2.97 (4H,q, J=7 Hz, 2×.CH$_2$.CH$_3$) and 3.35 (2H, septet, J=7 Hz, 2×CH$_3$.CH.CH$_3$).

m/e: 255 (M+).

Found: C, 70.69; H, 13.02; N, 16.46; C$_{15}$H$_{33}$N$_3$. Calculated: C, 70.53; H, 13.02; N, 16.45%.

EXAMPLE 6

Preparation of N-ethyl-N',N',N'',N''-tetraisopropyl guanidine

A solution of 2 ml phosgene (27.92 moles) in 10 ml of dry ether is added to 0.963 g of distilled, dry N,N,N',N'-tetraisopropyl guanidine (3.95 moles). A precipitate is rapidly formed and the mixture left standing at room temperature for 2 hours. The solvent and the excess phosgene are evaporated to give a white solid. The product is dissolved in 3 ml of distilled dry acetonitrile and 5 ml of dry ethylamine are added dropwise to the resulting solution at 0° C.

The mixture is heated to room temperature and the solvents are evaporated. The residue is triturated with ether and then treated with an excess of a 50% potassium hydroxide solution.

The product is extracted with ether and treated with brine.

After drying over anhydrous sodium sulfate, filtration and evaporation, 0.855 g of a pale yellow oil are obtained (yield 85%).

Drop-by-drop distillation in vacuo gives a colourless oil which has the following characteristics:

$v_{max}$ (film): 1610 cm$^{-1}$ (C=N).

$\delta$ (CDCl$_3$): 1.10 (3H, t, J=7 Hz, CH$_2$.CH$_3$) 1.15 (12H, d, J=7 Hz, 2×H$_3$C.CH.CH$_3$) 1.25 (12H, d, J=7 Hz, 2×H$_3$C.CH.CH$_3$) 3.18 (2H, q, J=7 Hz, CH$_2$.CH$_3$) 3.40 (2H, septet, J=7 Hz, 2×H$_3$C.CH.CH$_3$) and 3.76 (2H, septet, J=7 Hz, 2×H$_3$C.CH.CH$_3$).

m/e: 255 (M+) and 212 (M+—C₃H₇).

EXAMPLE 7

Preparation of N,N,N',N'-tetraisopropyl guanidine

A solution of 2 ml of phosgene (27.92 mmoles) in 10 ml of dry ether is added to 1.078 g of distilled, dry N,N,N',N'-tetraisopropyl thiourea (4.42 mmoles). A precipitate is rapidly formed and the mixture is left standing at room temperature for 2 h.

The solvent and the excess phosgene are evaporated, leaving a white solid. The product is dissolved in 2 ml of distilled dry acetonitrile and an excess of ammonia gas is injected into the solution at 0° C.

The solvent is evaporated, leaving a pale brown crystalline solid which is treated with a 50% aqueous potassium hydroxide solution and extracted with ether. The ethereal extracts are dried over anhydrous sodium sulfate, filtered and evaporated to give 0.874 g of a pale orange oil (yield 81%).

Drop-by-drop distillation in vacuo gives a colourless oil which corresponds to the title compound and which has the following properties:

$\nu_{max}$ (film): 3350–3100 (NH), 2970, 2930, 2870 (CH) and 1590 cm⁻¹ (C=N).

δ (CDCl₃): 1.20 (24H, d, J=7 Hz, 4×H₃C.CH.CH₃) 3.65 (4H, septet, J=7 Hz, 4×H₃C.CH.CH₃) and 5.55 (1H, br. N.H.) (the addition of D₂O causes the signal at δ 5.55 to disappear)

m/e: 227 (M+) and 184 (M+—C₃H₇).

EXAMPLE 8

Preparation of the methyl ester of hederagenin 0.41 g of hederagenin (0.87 mmole) is added to a solution of 0.199 g of N-t-butyl-N',N',N'',N''-tetramethylguanidine (1.16 mmoles) in 3 ml of dry dimethyl formamide. The mixture is heated until the solid dissolves and is then left to cool to room temperature.

1 ml of iodomethane (0.016 mole) is then added and the mixture is left standing at room temperature for 45 mins.

50 ml of water are then added to the reaction mixture and a white crystalline precipitate of hederagenin methyl ester is formed. The product is filtered and washed with water before being dried in vacuo to give 0.371 g of the title compound (yield 88%).

The product thus obtained has a melting point of 231°–233° C. (lit. 240° C.).

EXAMPLE 9

Preparation of the isopropyl ester of 1-adamantane carboxylic acid 0.289 g of 1-adamantane carboxylic acid are dissolved in 3 ml of distilled, dry benzene and 0.344 g of N-t-butyl-N',N',N'',N''-tetramethyl guanidine (2.01 mmoles). 1 ml of 2-iodopropane (10.02 mmoles) is added to the resulting solution and the mixture is left standing at room temperature. After about 5 minutes, a heavy yellow oil separates from the solution.

After 30 minutes, the solvent and the excess isopropyl iodide are evaporated to give a yellow oil. The product is distributed between ether and aqueous 1M hydrochloric acid and the aqueous phase is re-extracted with ether. The combined ethereal extracts are washed with water, a saturated aqueous sodium bicarbonate solution, water, a 5% aqueous sodium thiosulfate solution and finally with brine.

After drying over anhydrous sodium sulfate, filtration and evaporation, 0.32 g of a chromatographically homogeneous colourless oil which crystallises on standing is obtained (yield 91%).

This ester has a melting point of 29°–30° C.

EXAMPLE 10

Reaction of 3-β-cholestanyl tosylate with N-t-butyl-N',N'-diethyl-N'',N''-diisopropyl guanidine 0.269 g of 3-β-cholestanyl tosylate (0.50 mmole) is mixed with 1.34 g of N-t-butyl-N',N'-diethyl-N'',N''-diisopropyl guanidine (5.25 mmoles) and heated for 20 hours to 120° C. The product is then distributed between an excess of aqueous 1M hydrochloric acid and ether. The aqueous phase is re-extracted with ether and the combined extracts are washed with water, a saturated aqueous sodium bicarbonate solution, water and finally with brine.

After drying over anhydrous sodium sulfate, filtration and evaporation, a colourless oil is obtained. The product is purified by column chromatography on silica gel (eluent: ether/hexane 1:4) to give a mixture of Δ-2-cholestene and Δ-3-cholestene in the form of a white crystalline solid (0.145 g, yield 79%).

Crystallisation in a mixture of ethyl acetate and methanol gives long needles having the following characteristics:

Mp.: 68°–71° C. (lit. 67°–68° C.).

$[\alpha]_D^{20}$ = +58 (C1.1% of CHCl₃) (lit. +62, 4.9% in CHCl₃).

EXAMPLE 11

Reaction of ethyl acetoacetate with N-t-butyl-N',N',N'',N''-tetramethyl guanidine/iodomethane (A) A solution of 1.35 g of N-t-butyl-N',N',N'',N''-tetramethyl guanidine (7.89 mmoles) in 3 ml of distilled, dry ether is added to a solution of 1.023 g of distilled ethyl acetoacetate (7.87 mmoles) in 3 ml of distilled dry ether. 1 ml of iodomethane (16.1 mmoles) is added dropwise to the cooled mixture and the product is heated to room temperature and then left standing for 1 hour.

The mixture is filtered and the residue is washed with ether. The filtrate is evaporated to give 0.94 g of mono-C-methylated ethyl acetoacetate (yield 83%) containing less than 5% of dimethylated derivatives (NMR-spectroscopy).

(B) The 0.94 g of the above product are dissolved in 3 ml of distilled anhydrous ether and a solution of 1.50 g of N-t-butyl-N',N',N'',N''-tetramethylguanidine (8.77 mmoles) in 3 ml of distilled dry ether is added to the resulting solution. 2 ml of iodomethane (32.2 moles) are then added and the mixture left standing for 2 hours.

The product is distributed between ether and water. The ethereal extracts are washed with brine, dried over anhydrous sodium sulfate, filtered and evaporated to give 0.98 g of a colourless oil (yield 87%) of di-C-methylated compound and 13% of the starting compound (NMR-spectroscopy).

EXAMPLE 12

Reaction of 2,6-dimethyl phenol with N-t-butyl-N',N',N'',N''-tetramethyl guanidine/iodomethane 0.547 g of N-t-butyl-N',N',N'',N''-tetramethyl guanidine (3.20 mmoles) and then 1 ml of iodomethane (16.1 mmoles) are added to a solution of 0.349 g of 2,6-dimethylphenol (2.86 mmoles) in 2 ml of anhydrous ether.

After 30 minutes, the solvents are evaporated and the product is distributed between ether and an aqueous 1M hydrochloric acid solution. The ethereal extract is dried over anhydrous sodium sulfate, filtered and evaporated to give 0.31 g of 2,6-dimethyl anisole in the form of a pale yellow chromatographically homogeneous oil (NMR, IR, TLC); yield 80%.

We claim:

1. A highly sterically hindered guanidine of formula I

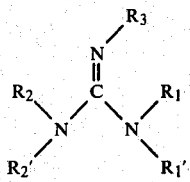
(I)

in which: $R_1$, $R_1'$, $R_2$, $R_2'$ and $R_3$ independently represent a hydrogen atom, a methyl, ethyl, isopropyl or tertiary butyl radical, $R_1$, $R'_1$, $R_2$, $R'_2$ and $R_3$ together containing in all at least 8 carbon atoms, with the proviso that when the four radicals $R_1$, $R_1'$, $R_2$, $R_2'$, all represent a methyl radical or all represent an ethyl radical, then $R_3$ is not a tertiary butyl radical.

2. A high sterically hindered guanidine according to claim 1, which is:
N-t-butyl-N',N'-diethyl-N'',N'''-diisopropylguanidine,
N-ethyl-N',N',N'',N''-tetraisopropylguanidine,
N,N,N',N'-tetraisopropylguanidine, or
N-t-butyl-N',N',N'',N''-tetraisopropylguanidine.

3. A process according to claim 1, in which the guanidine of formula:

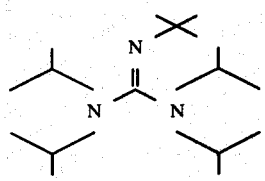

is prepared by reacting t-butylamine with an appropriate compound corresponding to formula III in the presence of n-butyllithium.

4. A process for the preparation of a guanidine according to claim 1, said process selected from
(a) the process, in which $R_1$, $R'_1$, $R_2$ and $R'_2$ are all $C_{3-6}$ alkyl radicals, by the action of phosgene on a thiourea of formula IV:

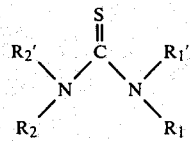
(IV)

in a solvent to obtain a Vilsmeier salt of formula III:

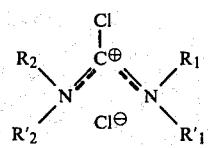
(III)

and reacting an amine of formula II:

$R_3NH_2$ (II)

with said Vilsmeier salt, and
(b) the process in which $R_1$, $R'_1$, $R_2$ and $R'_2$ are all methyl or ethyl, by the action of phosgene on a urea of formula V:

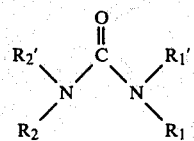
(V)

in a solvent to obtain a Vilsmeier salt of formula III, and reacting the amine of formula II:

$R_3NH_2$ (II)

with said Vilsmeier salt.

5. In a process of chemical synthesis using a highly sterically hindered base the improvement comprising the use of a guanidine of formula:

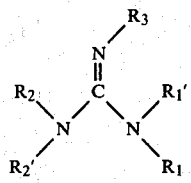
(I)

in which $R_1$, $R'_1$, $R_2$, $R'_2$ and $R_3$ independently represent a $C_1-C_6$ alkyl radical, in addition to which $R_3$ may represent a hydrogen atom, the alkyl radicals together containing in all at least 8 carbon atoms, as a highly sterically hindered base.

* * * * *